(12) United States Patent
Sasai et al.

(10) Patent No.: US 12,029,801 B2
(45) Date of Patent: Jul. 9, 2024

(54) SUNSCREEN MULTILAYER PARTICLE

(71) Applicant: L'OREAL, Paris (FR)

(72) Inventors: Jun Sasai, Kanagawa (JP); Toshifumi Shiroya, Kanagawa (JP)

(73) Assignee: L'OREAL, Paris (FR)

( * ) Notice: Subject to any disclaimer, the term of this patent is extended or adjusted under 35 U.S.C. 154(b) by 92 days.

(21) Appl. No.: 17/609,531

(22) PCT Filed: May 7, 2020

(86) PCT No.: PCT/JP2020/019171
§ 371 (c)(1),
(2) Date: Nov. 8, 2021

(87) PCT Pub. No.: WO2020/226184
PCT Pub. Date: Nov. 12, 2020

(65) Prior Publication Data
US 2022/0211588 A1 Jul. 7, 2022

(30) Foreign Application Priority Data

May 9, 2019 (JP) ................. 2019-088920

(51) Int. Cl.
*A61K 8/02* (2006.01)
*A61K 8/25* (2006.01)
*A61K 8/29* (2006.01)
*A61Q 17/04* (2006.01)

(52) U.S. Cl.
CPC .............. *A61K 8/0245* (2013.01); *A61K 8/25* (2013.01); *A61K 8/29* (2013.01); *A61Q 17/04* (2013.01); *A61K 2800/26* (2013.01); *A61K 2800/63* (2013.01); *A61K 2800/651* (2013.01); *A61K 2800/805* (2013.01)

(58) Field of Classification Search
CPC ............ A61K 2800/26; A61K 2800/63; A61K 8/0258
See application file for complete search history.

(56) References Cited

U.S. PATENT DOCUMENTS 4,168,986 A * 9/1979 Venis, Jr. ............ C23C 14/0005
106/436

FOREIGN PATENT DOCUMENTS

| JP | H08-268707 A | 10/1996 | |
|----|--------------|---------|---|
| JP | 2003-171575 A | 6/2003 | |
| JP | 2014-000811 A | 1/2014 | |
| WO | 2006/063949 A1 | 6/2006 | |
| WO | 2009/126722 A1 | 10/2009 | |
| WO | 2014/150846 A1 | 9/2014 | |
| WO | WO-2014150846 A1 * | 9/2014 | ............. C08K 3/013 |

OTHER PUBLICATIONS

PCT, International Search Report for the corresponding patent application No. PCT/JP2020/019171, dated Nov. 4, 2020.
Japanese Patent Office, "Decision to Grant a Patent", mailed Feb. 13, 2024 for corresponding Japanese Patent Application No. 2019-088920, together with English translation, 5 pages.

* cited by examiner

*Primary Examiner* — Mark V Stevens
(74) *Attorney, Agent, or Firm* — LUCAS & MERCANTI, LLP

(57) ABSTRACT

The present invention relates to a multilayer UV filter particle, comprising: an odd number of alternating layers of high and low refractive index materials, wherein each layer has a refractive index that differs from that of adjacent layers by at least 0.2, the total number of layers is at least 9, and the particle does not contain a substrate. The particle according to the present invention can have a good UV filtering effect.

14 Claims, 2 Drawing Sheets

Cross-Section TEM Image of Example 4

SUNSCREEN MULTILAYER PARTICLE

CROSS REFERENCE TO RELATED APPLICATION

This Application is a 371 of PCT/JP2020/019171 filed on May 7, 2020 which, in turn, claimed the priority of Japanese Patent Application No. 2019-088920 filed on May 9, 2019, and both applications are incorporated herein by reference.

TECHNICAL FIELD

The present invention relates to a UV filtering particle having a multilayer structure, a method for manufacturing the same, and the cosmetic process using the same.

BACKGROUND ART

As a material for filtering UV rays, various types of UV filters are known in the art. Such a material includes, for example, inorganic UV filters, such as titanium dioxide and zinc oxide, and organic UV filters, such as benzophenone derivatives and cinnamic derivatives. Among UV filter materials, a multilayer particle is also known to filter out UV rays efficiently by an interference effect.

To date, various documents regarding multilayer interference particles have been published. For example, WO 2014/150846 discloses a pigment including a platy substrate or uniform platy substrate coated with an odd number of layers of alternating layers of high or low refractive index material, wherein each layer has a refractive index that differs from that of adjacent layers by at least 0.2; and the pigment has from about 40 to about 100% reflectance of light having a wavelength of 280 nm to 400 nm. Also, JP-A-2003-171575 discloses a laminated interference UV shielding pigment which comprises a flaky or planer pigment coated with alternating layers having at least three layers of a metal oxide having a high refractive index and a metal oxide having a low refractive index. In addition, JP-A-2014-811 discloses a method for manufacturing a stand-alone multilayer thin film having three or more layers including the following steps: providing a substrate; depositing a sacrificial layer onto the substrate; depositing a multilayer thin film onto the sacrificial layer; and exposing the substrate, which has the sacrificial layer and the thin film, to chemical solutions that react with the sacrificial layer, thereby separating an intact multilayer thin film from the substrate.

However, there is still a need to provide a UV filer material which is able to reflect only UV rays with a very narrow cut-off transition range and to have a high transmittance region in visible wavelengths. Furthermore, there is a need to provide a UV filter material which is designed to be able to cut only target light such as UV rays and blue light.

DISCLOSURE OF INVENTION

An objective of the present invention is to provide a multilayer UV filter particle which is able to reflect only UV rays with a very narrow cut-off transition range and to have a high transmittance region in visible wavelengths, as well as designed so as to cut off only target light.

The above objective of the present invention can be achieved by a multilayer UV filter particle, comprising:
an odd number of alternating layers of high and low refractive index materials,
wherein each layer has a refractive index that differs from that of adjacent layers by at least 0.2, the total number of layers is at least 9, and the particle does not contain a substrate.

The high refractive index material may have a refractive index of larger than 1.7, preferably larger than 1.8, more preferably larger than 1.9, even more preferably larger than 2.0, and in particular larger than 2.1.

The low refractive index material may have a refractive index of lower than 1.65, preferably lower than 1.60, and more preferably lower than 1.55.

Each layer may have a refractive index that differs from that of the adjacent layers by at least 0.4, more preferably at least 0.6, and even more preferably at least 0.8.

The high and low refractive index materials may be metal oxides.

The thickness of the layer of the high refractive index material may range from 3 to 100 nm, preferably from 4 to 80 nm, and more preferably from 5 to 70 nm.

The thickness of the layer of the low refractive index material may range from 10 to 150 nm, preferably from 20 to 130 nm, and more preferably from 30 to 120 nm.

The particle may be formed with only the alternating layers of high and low refractive index materials.

The layers may be formed by a vapor deposition method.

The particle may exhibit 15 nm or less of a cut-off transition width, and more preferably 12 nm or less of a cut-off transition width.

The present invention also relates to a method for preparing the multilayer UV filter particle comprising steps of
preparing a substrate;
preparing a sacrificial layer on the substrate;
depositing an odd number of alternating layers of high and low refractive index materials on the sacrificial layer to prepare a multilayer structure;
detaching the multilayer structure from the sacrificial layer; and
pulverizing the multilayer structure to obtain the multilayer UV filter particle,
wherein each layer in the multilayer structure has a refractive index that differs from that of adjacent layers by at least 0.2, and the total number of layers in the multilayer structure is at least 9.

The deposition step may be performed using a vapor deposition method

The present invention also relates to a composition for topical use for keratinous substances, comprising the particle as an active ingredient.

The composition can be in the form of a powdery composition or a liquid composition.

The present invention also relates to a cosmetic use of the multilayer UV filter particle as an active ingredient to cut off UV rays.

BRIEF DESCRIPTION OF DRAWINGS

FIG. 1(a) represents the result of a transmittance of the particle. FIG. 1(b) represents the result of a differential curve of the transmittance according to FIG. 1(a). FIG. 1(c) represents an approximating curve (dotted curve) obtained by fitting a Gaussian least square method to the differential curve according to FIG. 1(b). The wavelength of a peak position (dot-line) in FIG. 1(c) represents a cut-off wavelength of the particle. A width at a half height of the peak is defined as "cut-off transition width".

BEST MODE FOR CARRYING OUT THE INVENTION

Figure 1:
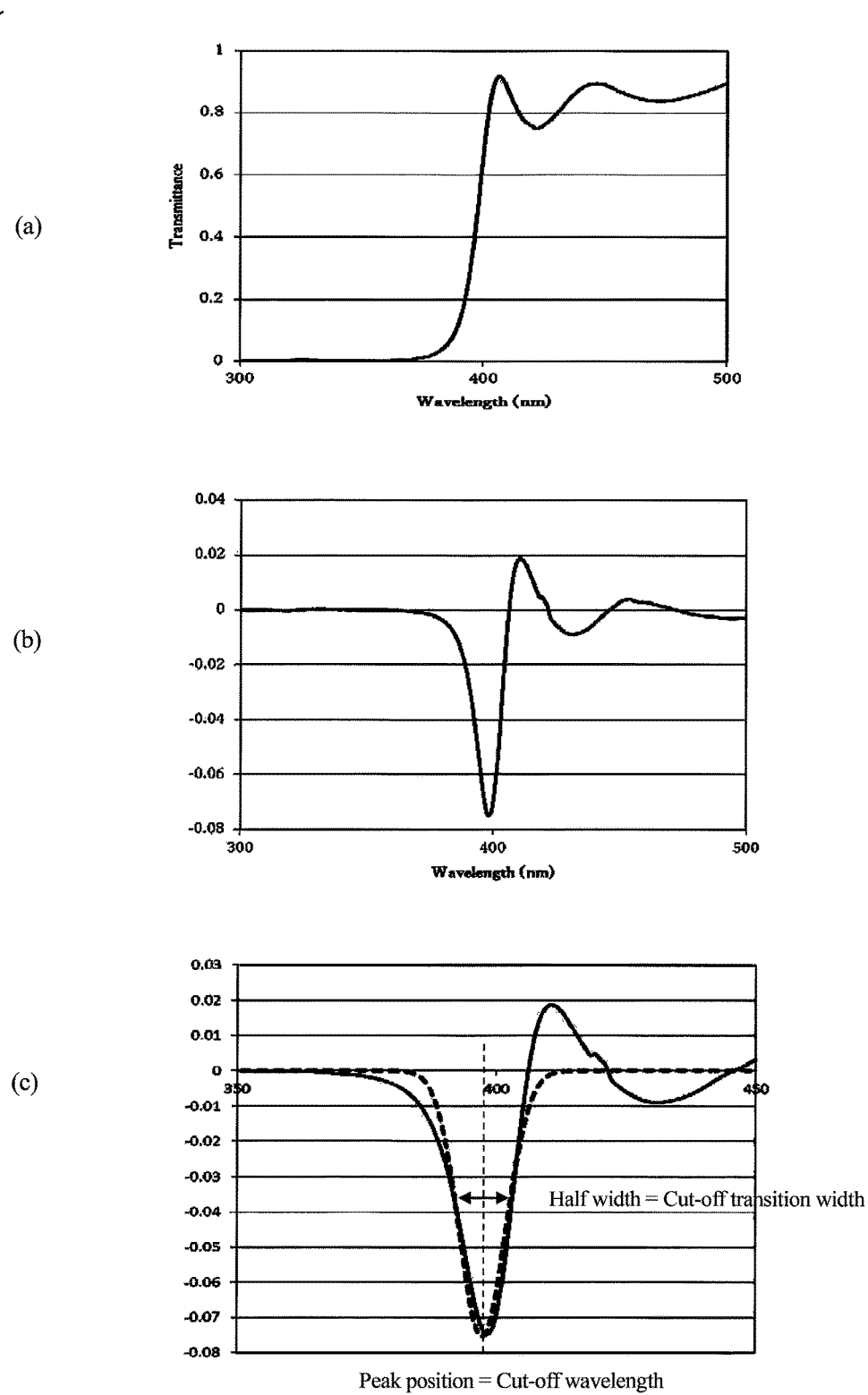
FIG. 1 shows one example of the measurement of a "cut-off transition width" of an exemplary particle.

After diligent research, the inventors have discovered that it is possible to provide a UV filter material having properties of reflecting UV light with a very narrow cut-off transition range, of having a high transmittance region in visible wavelengths, as well as being able to be designed so as to reflect only target light by a multilayer particle having at least 9 layers which does not include a substrate.

Thus, the present invention relates to a multilayer UV filter particle, comprising:
- an odd number of alternating layers of high and low refractive index materials,
- wherein each layer has a refractive index that differs from that of adjacent layers by at least 0.2, the total number of layers is at least 9, and the particle does not contain a substrate.

Hereinafter, the particle, composition, process and use, according to the present invention will be explained in a more detailed manner.

[Particle]

The present invention is directed to a multilayer UV filter particle, which comprises an odd number of alternating layers of high and low refractive index materials, wherein each layer has a refractive index that differs from that of adjacent layers by at least 0.2, the total number of layers is at least 9, and the particle does not contain a substrate.

The term "UV" here comprises the UV-B region (260-320 nm in wavelength), the UV-A region (320-400 nm in wavelength), and the high energy visible light region (400-450 nm in wavelength). Therefore, a UV filter means any material which has filtering effects in the wavelength of UV rays, in particular the UV-A, UV-B, and high energy visible light regions.

The multilayer UV filter particle according to the present invention can be designed to be active in the wavelength of the target length by modifying its structure and material. Therefore, the multilayer UV filter particle can be active in desired UV-A, UV-B, and high energy visible light regions.

The multilayer UV filter particle may be of any shape: platelet-shaped, spherical or oblong, irrespective of the crystallographic form.

The average particle size of the multilayer UV filter particle is not limited, but in general is 50 μm or less, preferably 30 μm or less, and more preferably 20 μm or less. The average particle size of the multilayer UV filter particle is 0.2 μm or more, preferably 0.5 μm or more, and more preferably 1 μm or more. The term "average primary particle size" used herein represents a number-average size mean diameter which is given by the statistical particle size distribution to half of the population, referred to as D50. For example, the number-average size mean diameter can be measured by a laser diffraction particle size distribution analyzer, such as Mastersizer 2000 by Malvern Corp.

In one embodiment of the present invention, the multilayer UV filter particle is in platy form or in a film form. In this case, the multilayer UV filter particle may have a thickness ranging from 0.1 to 10 mm, preferably from 0.2 to 6 mm, and more preferably from 0.3 to 3 mm. For the purpose of the present invention, the term "thickness" here means a length in a laminating direction of the layers in the particle.

The particle according to the present invention has a multilayer structure. The total number of layers is odd and is at least 9. The upper limit of the total number of layers is not limited, but in general is at most 80, and preferably at most 60.

The multilayer structure of the particle according to the present invention comprises alternating layers of high and low refractive index materials. That is, the multilayer structure of the particle according to the present invention comprises alternating layers of high refractive index layers, which are made of a high refractive index material, and low refractive index layers, which are made of a low refractive index material.

The thickness of the high refractive index layer is not limited, but in general is at least 3 nm, preferably at least 4 nm, and more preferably at least 5 nm, and less than 100 nm, preferably less than 80 nm, and more preferably less than 70 nm. Therefore, the thickness of the high refractive index layer may range from 3 to 100 nm, preferably from 4 to 80 nm, and more preferably from 5 to 70 nm.

The thickness of the low refractive index material is not limited, but in general is at least 10 nm, preferably at least 20 nm, and more preferably at least 30 nm, and less than 150 nm, preferably less than 130 nm, and more preferably less than 120 nm. Therefore, the thickness of the low refractive index layer may range from 10 to 150 nm, preferably from 20 to 130 nm, and more preferably from 30 to 120 nm.

In the particle according to the present invention, each layer has a refractive index that differs from that of the adjacent layers by at least 0.2. That is, the difference between the high refractive index material and the low refractive index material in the present invention is at least 0.2. Preferably, each layer in the particle has a refractive index that differs from that of the adjacent layers by at least 0.4, more preferably at least 0.6, and even more preferably at least 0.8.

In one embodiment of the present invention, the layers of the high refractive index material have a refractive index of larger than 1.7, preferably larger than 1.8, more preferably larger than 1.9, even more preferably larger than 2.0, and in particular larger than 2.1. The upper limit of the refractive index of the high refractive index material is not limited, but in general is less than 5.0, preferably less than 4.0, and more preferably less than 3.0.

Materials suitable for the high refractive index material include, but are not limited to, titanium dioxide ($TiO_2$, 2.43) vacuum deposited, cerium oxide ($CeO_2$, 2.53), niobium oxide ($Nb_2O_3$, 2.4), niobium pentoxide ($Nb_2O_5$, 2.4), hafnium oxide ($HfO_2$, 1.9-2.0), zirconium oxide ($ZrO_2$, 2.36), alumina oxide ($Al_2O_3$, 1.75), yttrium oxide ($Y_2O_3$, 1.75), germanium (Ge, 4.0-5.0), chromium (Cr, 3.0), tellurium (Te, 4.6), tin sulfide (SnS, 2.6), gallium antimonite (GaSb, 4.5-5.0), indium arsenide (InAs, 4.0), chalcogenide glass (2.6), silicon (Si, 3.7), indium phosphate (InP, 3.5), tungsten (W, 2.5), gallium arsenate (GaAs, 3.53), gallium nitride (GaN, 2.5), gallium phosphate (GaP, 3.31), manganese (Mn, 2.5), vanadium (V, 3), arsenic selenide ($As_2Se_3$, 2.8), zinc telluride (ZnTe, 3.0), $CuAlSe_2$ (2.75), chalcogenide glass+Ag (3.0), zinc selenide (ZnSe, 2.5-2.6), zinc sulfate ($ZnSO_4$, 2.5-3.0), zinc sulfide (ZnS, 2.3), aluminium (Al, 2.0), and silicon nitride (SiN, 2.1).

The numerical value in parentheses represents the refractive index of the material. Two or more types of high refractive index materials may be used in combination. Preferably, the high refractive index material is selected from metal oxides, such as $TiO_2$, $CeO_2$, $Nb_2O_3$, $Nb_2O_5$, $HfO_2$, $Al_2O_3$, $Y_2O_3$, and $ZrO_2$.

In one embodiment of the present invention, the layers of the low refractive index material have a refractive index of at least 0.2 less than that of the high refractive index material. For example, the low refractive index material may have a refractive index of less than 1.65, preferably less than 1.60, and more preferably less than 1.55.

Materials suitable for the low refractive index material include, but are not limited to, inorganic materials, such as silica ($SiO_2$, 1.5), vacuum deposited silica ($SiO_2$, 1.46), indium tin oxide (ITO, 1.46), sodium aluminum fluoride ($Na_3AlF_6$, 1.6), magnesium fluoride ($MgF_2$, 1.37), lead fluoride ($PbF_2$, 1.6), potassium fluoride (KF, 1.5), lithium fluoride ($LiF_4$, 1.45), calcium fluoride ($CaF_2$, 1.43), barium fluoride ($BaF_2$, 1.5), strontium fluoride ($SrF_2$, 1.43), lithium fluoride (LiF, 1.39), aluminum arsenide (AlAs, 1.56), mica (1.56), and sodium fluoride (NaF, 1.5), and organic materials such as polyamide-imide (PEI, 1.6), polystyrene (PS, 1.6), polyether sulfone (PES, 1.55), polyethylene (1.5), PMMA (1.5), PKFE (1.6), polyallomer (PA, 1.492), polybutylene (1.50), fluorocarbon (FEP, 1.34), ionomers (1.51), polytetrafluro-ethylene (TFE, 1.35), nylon (PA) type II (1.52), acrylic multipolymer (1.52), chlorotrifluoro-ethylene (CTFE, 1.42), cellulose propionate (1.46), styrene butadiene (1.52-1.53), cellulose acetate butyrate (1.46-1.49), PVC (1.52-1.55), cellulose acetate (1.46-1.50), nylon (Polyamide) type 6/6 (1.53), methylpentene polymer (1.485), urea formaldehyde (1.54-1.58), acetal homopolymer (1.48), acrylics (1.49), styrene acrylonitrilecopolymer (1.56-1.57)), cellulose nitrate (1.49-1.51), ethyl cellulose (1.47), polypropylene (1.49), polysulfone (1.633), and polycarbonate. The numerical value in parentheses represents the refractive index of the material. Two or more types of low refractive index materials may be used in combination. Preferably, the low refractive index material is selected from metal oxides, such as $SiO_2$ and ITO, and fluorides, such as $Na_3AlF_6$, $MgF_2$, $PbF_2$, $CaF_2$, KF, LiF, $BaF_2$, NaF, and $SrF_2$, and in particular selected from metal oxides such as $SiO_2$ and ITO.

The particle according to the present invention does not contain a substrate. For the purpose of the present invention of the particle, the term "substrate" here means a substance which is in direct contact with the layers of the particle but can be thinner than the layer of the particle according to the present invention. In general, the substrate is platy and functions as a support for manufacturing the multilayer structure of the particle.

In one embodiment of the present invention, the particle is formed with only the alternating layers of high and low refractive index materials. That is, the particle comprises only the layers of a high refractive index material and a low refractive index material.

The multilayer UV filter particle according to the present invention can filter out UV rays with a very narrow cut-off transition range and have a high transmittance region in visible wavelengths. This property means that the particle according to the present invention has a UV filtering effect in a very specific rage of wavelengths, i.e. sharp UV-cut property, while maintaining a high transmittance region in visible wavelengths. Therefore, the present invention can provide a superior UV filtering effect and a transparent and natural appearance with a cosmetic composition when it is used in the cosmetic composition.

The property of the very specific UV filtering effect of the particle according to the present invention can be characterized by so-called "cut-off transition width" of the particle. The "cut-off transition width" can be obtained by measuring the transmittance of a particle, calculating a differential curve of the transmittance, fitting a Gaussian least square method to the differential curve, and then measuring the half width of a peak in the fitted curve by the Gaussian least square method.

FIG. 1 shows one example of the measurement of the "cut-off transition width" of a given particle. FIG. 1(a) shows the transmittance of the particle. FIG. 1(b) shows a differential curve of the transmittance according to FIG. 1(a). FIG. 1(c) shows an approximating curve (dotted curve) obtained by fitting a Gaussian least square method to the differential curve according to FIG. 1(b). The wavelength of a peak position (dot-line) in FIG. 1(c) represents a cut-off wavelength of the particle. The width at half height of the peak is defined as the "cut-off transition width". The narrower the cut-off transition width, the narrower the transition range from high transmittance in visible wavelength to low transmittance in UV.

The particle according to the present invention preferably exhibits a cut-off transition width of 15 nm or less, and more preferably a cut-off transition width of 12 nm or less.

In addition, the inventors of the present invention surprisingly found that the particle according to the present invention can be designed to protect a desired range of wavelengths by modifying the multilayer structure, i.e. the number of layers and thickness of each layers, and the composition of each layer, i.e. each layer having a high or low refractive index. Therefore, the multilayer UV filter particle can be active in a desired region in the UV-A, UV-B, and high energy visible light regions.

In one preferred embodiment of the present invention, the alternating layers of high and low refractive index materials of the particle are formed with a well-known vapor and liquid deposition method, such as chemical vapor deposition, physical vapor deposition, spray deposition, and mist deposition. The layer formed with such deposition method can have a precise and even thickness.

Therefore, the present invention also relates to a multilayer UV filter particle, comprising: an odd number of alternating layers of high and low refractive index materials formed by a vapor deposition method, wherein each layer has a refractive index that differs from that of adjacent layers by at least 0.2, the total number of layers is at least 9, and the particle does not contain a substrate.

[Preparation]

The present invention also relates to a method for preparing the multilayer UV filter particle according to the present invention.

The method for preparing the multilayer UV filter particle according to the present invention comprises steps of
  preparing a substrate;
  preparing a sacrificial layer on the substrate;
  depositing an odd number of alternating layers of high and low refractive index materials on the sacrificial layer to prepare a multilayer structure;
  detaching the multilayer structure from the sacrificial layer; and
  pulverizing the multilayer structure to obtain the multilayer UV filter particle,
  wherein each layer in the multilayer structure has a refractive index that differs from that of adjacent layers by at least 0.2, and the total number of layers in the multilayer structure is at least 9.

The step of preparing a substrate is a step to prepare a substrate as a support for manufacturing the multilayer structure of the particle.

The substrate in the preparation process is not limited as long as it can be used as a support for manufacturing the multilayer structure of the particle. In general, a platy material, such as a glass plate and plastic film, can be used as the substrate.

The step of preparing a sacrificial layer on the substrate is a step to put a sacrificial layer on one side of the substrate.

The "sacrificial layer" here means any material which can function as a support for manufacturing the multilayer structure of the particle and can be detached from the multilayer structure after the multilayer structure was prepared. In general, the sacrificial layer is in the form of a film, tape, or sheet.

The material of the sacrificial layer is not limited as long as it fulfills the above objective. Suitable materials for the sacrificial layer include, for example, an organic film such as a polyimide film and polyester film, and a soluble material in water, a solvent, an acidic solution, or the like, for example, a soluble polymer in water, a solvent, an acidic solution, or the like, preferably water soluble polymer, such as polyvinyl alcohol and polyacrylamide.

The step of depositing an odd number of alternating layers of high and low refractive index materials on the sacrificial layer to prepare a multilayer structure is a step of manufacturing the multilayer structure of the particle according to the present invention comprising the alternating layers of high and low refractive index materials, which are explained above.

The deposition step can be performed using a well-known vapor and liquid deposition methods, such as chemical vapor deposition, physical vapor deposition, spray deposition, and mist deposition, or wet-chemical process known in the art. The vapor deposition method is very advantageous since it can produce layers with a precise and even thickness. The deposition step is repeated until the multilayer structure comprising at least 9 layers is obtained. The high and low refractive index materials are as defined above.

The step of detaching the multilayer structure from the sacrificial layer is a step to separate the obtained multilayer structure from the sacrificial layer.

When the material of the sacrificial layer is an organic polymer, the multilayer structure can be detached physically, for example, by bending the sacrificial layer. When the material of the sacrificial layer is a soluble material, the multilayer structure can be detached by dissolving the sacrificial layer. Therefore, a suitable soluble material for the sacrificing layer is a water soluble material, such as polyvinyl alcohol, since the multilayer structure can be detached by dissolving the sacrificial layer in water, which is milder than a solvent or an acidic solution.

The step of pulverizing the multilayer structure to obtain the multilayer UV filter particle is a step to pulverizing the detached multilayer structure to obtain the particle according to the present invention.

Methods to pulverize the multilayer structure are not limited as long as a multilayer structure in the form of a powder is obtained. Exemplary pulverizing methods include, for example, grinding with equipment, such as a pestle and a spatula, and using a mill.

[Cosmetic Composition]

The present invention also relates to a composition, preferably a cosmetic composition comprising the multilayer UV filter particle according to the present invention. The composition according to the present invention can be a powdery composition, for example, a powdery composition in the form of a compact or pressed powder, blusher or a loose powder, or a liquid composition, for example, a liquid composition in a form such as an emulsion (O/W or W/O form), an aqueous gel, an aqueous solution, a lotion, a milky lotion, a cream, a foam, a paste, a serum or the like. The particle according to the present invention functions in the composition as an active ingredient to filter out UV rays.

When the composition is a powdery composition, the multilayer UV filter particle can generally be present in the composition in proportions ranging from 1% to 40% by weight, preferably ranging from 5% to 30% by weight, and more preferably 10% to 25% by weight, with respect to the total weight of the composition.

When the composition is a liquid composition, the multilayer UV filter particle can generally be present in the composition in proportions ranging from 1% to 30% by weight, preferably ranging from 3% to 20% by weight, and more preferably 5% to 15% by weight, with respect to the total weight of the composition.

Since the particle according to the present invention can be designed to protect a desired range of wavelengths by modifying the multilayer structure, the composition can include two or more kinds of the multilayer UV filter particles in combination, which are designed to reflect different UV wavelengths. For example, it is preferred that the composition include a multilayer UV filter particle which is designed to cut off UV rays in the UV-B region and a multilayer UV filter particle which is designed to cut off UV rays in the UV-A region in combination. Accordingly, it is possible that the composition according to the present invention filters out UV rays in both of the UV-A and UV-B regions using only the particle according to the present invention.

Therefore, in one embodiment of the present invention, the composition does not include a UV filter material other than the multilayer UV filter particle according to the present invention. In another embodiment of the present invention, the composition does not include an organic UV filter. In yet another embodiment of the present invention, the composition does not include an inorganic UV filter other than the multilayer UV filter particle according to the present invention.

The composition according to the present invention may be intended for use as a cosmetic topical composition. Thus, the composition according to the present invention may be intended for application onto a keratinous substance. Keratinous substance here means a material containing keratin as a main constituent element, and examples thereof include the skin, scalp, nails, lips, hair, and the like. In particular, the composition according to the present invention may be a skin sun care cosmetic composition for protecting skin from UV rays.

[Process and Use]

The particle according to the present invention can be used as an active ingredient to cut off UV rays. Therefore, the present invention also relates to a non-therapeutic process, such as a cosmetic process, or a use of the multilayer UV filter particle as an active ingredient to cut off UV rays.

EXAMPLES

The present invention will be described in more detail by way of examples which however should not be construed as limiting the scope of the present invention.

[Particle]

The following particles according to Examples 1 to 7 (Ex. 1 to 7) and Comparative Examples 1 and 2 (Comp. Ex. 1 and 2), shown in Table 1, were prepared by the following procedure.

[Preparation Procedure]

(1) A glass plate was prepared as a substrate.

(2) Polyimide tape was placed on one side of the glass plate.

(3) A predetermined number of alternating layers of $TiO_2$ and $SiO_2$ were laminated on the polyimide film by vacuum vapor deposition, to prepare a multilayer structure in the form of a film.

The number of layers of each of Examples 1 to 7 and Comparative Examples 1 and 2 is described in Table 1.

(4) The obtained multilayer structure was detached from the polyimide tape by bending the tape.

All of the pieces of the cracked multilayer structure were washed with water and were collected by filtration.

(5) The detached multilayer structure was pulverized by grinding with a spatula to obtain the multilayer UV filter particle.

[Evaluation]

(Thickness Measurement)

The thickness of each of the layers of the multilayer structure according to each of Examples 1 to 7 and Comparative Examples 1 and 2 was measured by observing a cross-section of each of the samples using a transmission electron microscope (TEM). The samples were prepared by cutting each of the samples into a very thin piece by a focus ion beam (FIB). The compositions of each of the layers according to Examples 1 to 7 and Comparative Examples 1 and 2 were confirmed by energy dispersive X-ray spectrometry (EDS).

Figure 2:
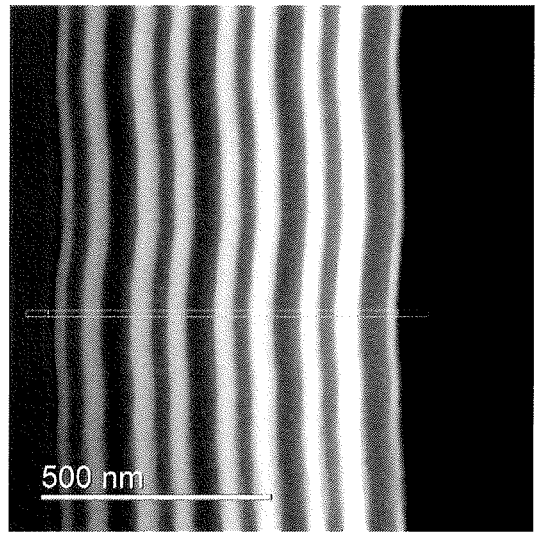
FIG. 2 shows a cross-section of a multilayer structure according to Example 4 observed by TEM as one exemplary reference.

FIG. 2 shows a cross-section of the multilayer structure according to Example 4 observed by TEM as one exemplary reference.

The composition and the measured thickness of each of the layers of the particle according to each of Examples 1 to 7 and Comparative Examples 1 and 2 are summarized in Table 1.

(UV Filtering Property)

1 mg of the particle according to each of Examples 1 to 7 and Comparative Examples 1 and 2 was dispersed in 100 μL of ion exchanged water to obtain a suspension, and the whole amount of the suspension was poured onto a slide glass with a pipette. The slide glass was dried over night to remove water and to fix the particle on the surface of the slide glass. The obtained spot of the sample had a diameter of about 2 cm. The transmittance of the spot was measured with a spectrophotometer (JASXO V-550) using an integrating sphere. The "cut-off transition width" was obtained by calculating a differential curve of the transmittance, fitting a Gaussian least square method to the differential curve, and then measuring the half width of a peak in the fitted curve by the Gaussian least square method, as explained in FIG. 1 and the specification.

(SPF Value)

The in vitro SPF value of the particle was measured using an ultraviolet transmittance analyzer (Labsphere UV-2000S).

The UV filtering property and SPF value of the particle according to each of Examples 1 to 7 and Comparative Examples 1 and 2 are summarized in Table 2. In Table 2, "Target cut-off wavelength (nm)" in item [A] means the target cut-off wavelength value which was defined before manufacturing. "Cut-off wavelength of particles (nm)" in item [B] means an actual measurement value of the cut-off wavelength of the particle. Therefore, "Difference of [A]-[B]" in Table 2 indicates the difference between the target value and the measured value of the cut-off wavelength.

TABLE 1

| Number of Layers | Composition | Com. Ex. 1 | Comp. Ex. 2 | Ex. 1 | Ex. 2 | Ex. 3 |
|---|---|---|---|---|---|---|
| 1 | $TiO_2$ | 21 | 34 | 14 | 10 | 26 |
| 2 | $SiO_2$ | 47 | 34 | 68 | 79 | 57 |
| 3 | $TiO_2$ | 40 | 67 | 33 | 28 | 54 |
| 4 | $SiO_2$ | 49 | 36 | 48 | 54 | 33 |
| 5 | $TiO_2$ | 21 | 22 | 30 | 33 | 42 |
| 6 | $SiO_2$ | — | — | 49 | 68 | 59 |
| 7 | $TiO_2$ | — | — | 30 | 19 | 49 |
| 8 | $SiO_2$ | — | — | 59 | 76 | 40 |
| 9 | $TiO_2$ | — | — | 15 | 28 | 40 |
| 10 | $SiO_2$ | — | — | — | 51 | 60 |
| 11 | $TiO_2$ | — | — | — | 33 | 40 |
| 12 | $SiO_2$ | — | — | — | 82 | 36 |
| 13 | $TiO_2$ | — | — | — | 11 | 46 |
| 14 | $SiO_2$ | — | — | — | — | 60 |
| 15 | $TiO_2$ | — | — | — | — | 44 |
| 16 | $SiO_2$ | — | — | — | — | 31 |
| 17 | $TiO_2$ | — | — | — | — | 26 |

| Number of Layers | Composition | Ex. 4 | Ex. 5 | Ex. 6 | Ex. 7 |
|---|---|---|---|---|---|
| 1 | $TiO_2$ | 7 | — | 19 | 20 |
| 2 | $SiO_2$ | 86 | 115 | 56 | 74 |
| 3 | $TiO_2$ | 27 | 54 | 36 | 54 |
| 4 | $SiO_2$ | 62 | 39 | 56 | 56 |
| 5 | $TiO_2$ | 27 | 47 | 39 | 38 |
| 6 | $SiO_2$ | 62 | 66 | 59 | 70 |
| 7 | $TiO_2$ | 27 | 42 | 39 | 49 |
| 8 | $SiO_2$ | 62 | 54 | 59 | 56 |
| 9 | $TiO_2$ | 27 | 50 | 42 | 43 |
| 10 | $SiO_2$ | 62 | 61 | 58 | 68 |
| 11 | $TiO_2$ | 27 | 41 | 42 | 45 |
| 12 | $SiO_2$ | 62 | 61 | 62 | 53 |
| 13 | $TiO_2$ | 27 | 50 | 38 | 43 |
| 14 | $SiO_2$ | 62 | 54 | 63 | 61 |
| 15 | $TiO_2$ | 27 | 42 | 42 | 37 |
| 16 | $SiO_2$ | 62 | 66 | 59 | 58 |
| 17 | $TiO_2$ | 18 | 47 | 41 | 41 |
| 18 | $SiO_2$ | 86 | 39 | 61 | 60 |
| 19 | $TiO_2$ | 6 | 54 | 43 | 42 |
| 20 | $SiO_2$ | — | 115 | 58 | 60 |
| 21 | $TiO_2$ | — | — | 41 | 43 |
| 22 | $SiO_2$ | — | — | 63 | 67 |
| 23 | $TiO_2$ | — | — | 41 | 37 |
| 24 | $SiO_2$ | — | — | 57 | 66 |
| 25 | $TiO_2$ | — | — | 43 | 39 |
| 26 | $SiO_2$ | — | — | 61 | 61 |
| 27 | $TiO_2$ | — | — | 40 | 41 |
| 28 | $SiO_2$ | — | — | 50 | 63 |
| 29 | $TiO_2$ | — | — | 45 | 45 |
| 30 | $SiO_2$ | — | — | 76 | 59 |
| 31 | $TiO_2$ | — | — | 15 | 48 |
| 32 | $SiO_2$ | — | — | — | 65 |
| 33 | $TiO_2$ | — | — | — | 48 |
| 34 | $SiO_2$ | — | — | — | 66 |
| 35 | $TiO_2$ | — | — | — | 47 |
| 36 | $SiO_2$ | — | — | — | 68 |
| 37 | $TiO_2$ | — | — | — | 47 |
| 38 | $SiO_2$ | — | — | — | 71 |
| 39 | $TiO_2$ | — | — | — | 47 |
| 40 | $SiO_2$ | — | — | — | 69 |
| 41 | $TiO_2$ | — | — | — | 48 |
| 42 | $SiO_2$ | — | — | — | 70 |
| 43 | $TiO_2$ | — | — | — | 48 |
| 44 | $SiO_2$ | — | — | — | 70 |
| 45 | $TiO_2$ | — | — | — | 47 |
| 46 | $SiO_2$ | — | — | — | 70 |
| 47 | $TiO_2$ | — | — | — | 47 |
| 48 | $SiO_2$ | — | — | — | 69 |
| 49 | $TiO_2$ | — | — | — | 49 |
| 50 | $SiO_2$ | — | — | — | 69 |
| 51 | $TiO_2$ | — | — | — | 43 |
| 52 | $SiO_2$ | — | — | — | 66 |
| 53 | $TiO_2$ | — | — | — | 53 |
| 54 | $SiO_2$ | — | — | — | 81 |
| 55 | $TiO_2$ | — | — | — | 18 |

TABLE 2

| | [A] Target cut-off wavelength (nm) | [B] Cut-off wavelength of particles (nm) | Difference of [A] − [B] (nm) | Cut-off transition width (nm) | in-vitro SPF |
|---|---|---|---|---|---|
| Comp. Ex. 1 | 406 | 438 | 32 | 19.2 | 61 |
| Comp. Ex. 2 | 453 | 480 | 27 | 31.7 | 36 |
| Ex. 1 | 393 | 405 | 12 | 9.0 | 177 |
| Ex. 2 | 401 | 404 | 3 | 7.0 | 408 |
| Ex. 3 | 378 | 377 | −1 | 10.2 | 288 |
| Ex. 4 | 400 | 404 | 4 | 4.2 | n.m. |
| Ex. 5 | 397 | 399 | 2 | 6.4 | n.m. |
| Ex. 6 | 400 | 407 | 7 | 4.8 | 834 |
| Ex. 7 | 461 | 462 | 1 | 8.7 | 971 |

"n.m." stands for "not measured"

The invention claimed is:

1. A multilayer UV filter particle, comprising:
    an odd number of alternating layers of high and low refractive index materials,
    wherein each layer has a refractive index that differs from that of adjacent layers by at least 0.2, the total number of layers is at least 9, and the particle does not contain a substrate,
    wherein the high refractive index material has a refractive index of larger than 1.7 and less than 5.0, the low refractive index material has a refractive index of lower than 1.65, and the high and low refractive index materials are metal oxides, and
    wherein the thickness of each of the layers of the high refractive index material ranges from 3 to 100 nm and the thickness of each of the layers of the low refractive index material ranges from 10 to 150 nm.

2. The particle according to claim 1, wherein the high refractive index material has a refractive index of larger than 1.8 and less than 5.0.

3. The particle according to claim 1, wherein the low refractive index material has a refractive index of lower than 1.60.

4. The particle according to claim 1, wherein each layer has a refractive index that differs from that of the adjacent layers by at least 0.4.

5. The particle according to claim 1, wherein the thickness of each of the layers of the high refractive index material ranges from 4 to 80 nm.

6. The particle according to claim 1, wherein the thickness of each of the layers of the low refractive index material ranges from 20 to 130 nm.

7. The particle according to claim 1, which is formed with only the alternating layers of high and low refractive index materials.

8. The particle according to claim 1, wherein the layers are formed by a vapor deposition method.

9. The particle according to claim 1, which exhibits a cut-off transition width of 15 nm or less.

10. A method for preparing the multilayer UV filter particle according to claim 1, comprising the steps of:
    preparing a substrate;
    preparing a sacrificial layer on the substrate;
    depositing an odd number of alternating layers of high and low refractive index materials on the sacrificial layer to prepare a multilayer structure;
    detaching the multilayer structure from the sacrificial layer; and
    pulverizing the multilayer structure to obtain the multilayer UV filter particle,
    wherein each layer in the multilayer structure has a refractive index that differs from that of adjacent layers by at least 0.2, and the total number of layers in the multilayer structure is at least 9,
    wherein the high refractive index material has a refractive index of larger than 1.7 and less than 5.0, the low refractive index material has a refractive index of lower than 1.65, and the high and low refractive index materials are metal oxides, and
    wherein the thickness of each of the layers of the high refractive index material ranges from 3 to 100 nm and the thickness of each of the layers of the low refractive index material ranges from 10 to 150 nm.

11. The method according to claim 10, wherein the deposition step is performed using a vapor deposition method.

12. A composition for topical use for keratinous substances, comprising the particle according to claim 1 as an active ingredient.

13. The composition according to claim 12, which is in the form of a powdery composition or a liquid composition.

14. A cosmetic method comprising:
    applying a composition to a keratinous substance, the composition comprising the multilayer UV filter particle according to claim 1 as an active ingredient to cut off UV rays.

* * * * *